US012599566B2

(12) United States Patent
Karan et al.

(10) Patent No.: US 12,599,566 B2
(45) Date of Patent: Apr. 14, 2026

(54) TITANIUM DIOXIDE FREE WHITE FILM COATING COMPOSITION, PROCESS FOR PREPARING THE SAME AND METHOD OF USE THEREOF

(71) Applicant: HERCULES LLC, Wilmington, DE (US)

(72) Inventors: Kapish Karan, Wilmington, DE (US); Ronald Hach, Wilmington, DE (US)

(73) Assignee: HERCULES LLC, Wilmington, DE (US)

( * ) Notice: Subject to any disclaimer, the term of this patent is extended or adjusted under 35 U.S.C. 154(b) by 777 days.

(21) Appl. No.: 17/764,520

(22) PCT Filed: Sep. 25, 2020

(86) PCT No.: PCT/US2020/052724
§ 371 (c)(1),
(2) Date: Mar. 28, 2022

(87) PCT Pub. No.: WO2021/062158
PCT Pub. Date: Apr. 1, 2021

(65) Prior Publication Data
US 2022/0347103 A1 Nov. 3, 2022

Related U.S. Application Data

(60) Provisional application No. 62/907,531, filed on Sep. 27, 2019.

(51) Int. Cl.
*A61K 9/28* (2006.01)
*C09D 101/28* (2006.01)

(52) U.S. Cl.
CPC .......... *A61K 9/2866* (2013.01); *A61K 9/2893* (2013.01); *C09D 101/284* (2013.01)

(58) Field of Classification Search
CPC . A61K 9/2866; A61K 9/2893; C09D 101/284
See application file for complete search history.

(56) References Cited

U.S. PATENT DOCUMENTS

| 4,931,286 A | 6/1990 | Johnson et al. |
| 5,248,516 A | 9/1993 | Wheatley et al. |
| 9,636,706 B2 | 5/2017 | Jiang et al. |
| 10,159,650 B2 | 12/2018 | Schad et al. |
| 2008/0069873 A1* | 3/2008 | Pearnchob .......... A61K 9/5073 |
| | | 424/459 |
| 2011/0280942 A1 | 11/2011 | Schad et al. |
| 2012/0195955 A1 | 8/2012 | Bryson et al. |
| 2014/0065232 A1 | 3/2014 | Bhargava et al. |
| 2018/0104191 A1 | 4/2018 | Zhu et al. |
| 2020/0140714 A1 | 5/2020 | Despax et al. |
| 2021/0100275 A1 | 4/2021 | Schad |

FOREIGN PATENT DOCUMENTS

| CA | 2732593 | | 2/2010 |
| CA | 3071047 | | 1/2019 |
| CN | 102295788 A | | 12/2011 |
| CN | 104204351 A | | 12/2014 |
| CN | 110248551 A | | 9/2019 |
| EP | 0551700 A1 | | 7/1993 |
| EP | 3339355 A1 | | 6/2018 |
| EP | 3621451 A1 | | 3/2020 |
| ES | 2261006 B1 | * | 11/2006 |
| JP | 2002-011526 A2 | | 1/2002 |
| JP | 2002-534373 A2 | | 10/2002 |
| JP | 2016-505242 A2 | | 2/2016 |
| JP | 2020-519271 A2 | | 7/2020 |
| JP | 2020-528065 A2 | | 9/2020 |
| JP | 2021-526506 A2 | | 10/2021 |
| WO | WO1991015548 A1 | | 10/1991 |
| WO | WO2018206709 A1 | | 11/2018 |
| WO | WO2019161402 A1 | | 8/2019 |

OTHER PUBLICATIONS

Villiers (2008) pp. 225-230.*
References cited in the International Search Report of International Application No. PCT/US20/052724.

* cited by examiner

*Primary Examiner* — Shirley V Gembeh
(74) *Attorney, Agent, or Firm* — Aseem V. Mehta; Nathalie Tietcheu

(57) ABSTRACT

The present application provides titanium dioxide free film coating compositions comprising a combination of a water soluble cellulose ether, a water soluble anionic cellulose ether, calcium carbonate and a plasticizer. The invention further provides a process for preparing the film coating compositions and a method of coating solid substrates with such coating compositions.

9 Claims, 4 Drawing Sheets

TABLET COATED WITH HPC

Poor opacity with edge chipping

COMPARISON IMAGES

Whiter

Existing Coatings with HPMC + Calcium Carbonate

Applicants Coatings with HPMC + NaCMC + Calcium Carbonate

TABLET WHITENESS COMPARISON (VISUAL)

TABLET WHITENESS COMPARISON (EXPERIMENTAL)

FILM COATING OPACITY

TABLET SURFACE ROUGHNESS & GLOSS EVALUATION

EFFECT OF PARTICLE SIZE OF CALCIUM CARBONATE ON APPLICANT'S COATINGS (BETTER OPACITY)

Particle Size ~ 0.7 Microns
Structure - Prismatic

Particle Size ~ 1.3 Microns
Structure - Scalenohedral

Particle Size ~ 2.0 Microns
Structure - Scalenohedral

 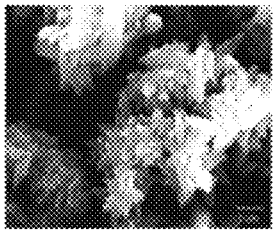 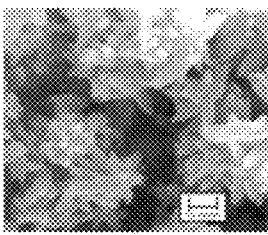

Better Opacity        Better Opacity

Fig. 7

EFFECT OF PARTICLE SIZE OF CALCIUM CARBONATE ON APPLICANT'S COATINGS (BETTER COVERAGE OF WHITENESS)

Fig. 8

TITANIUM DIOXIDE FREE WHITE FILM COATING COMPOSITION, PROCESS FOR PREPARING THE SAME AND METHOD OF USE THEREOF

FIELD OF THE INVENTION

This application relates to coating compositions, and more particularly, to titanium dioxide free white film coating compositions, a process for the preparation thereof and a method of coating solid substrates.

BACKGROUND OF THE INVENTION

Coatings play a major role in many industrial segments, including pharmaceutical, veterinary, agricultural, nutritional, automotive, biochemical, chemical, computer, consumer goods, foods, electronics, materials, and healthcare. The presence of coatings across so many application arts is due to the wide range of functionalities coatings impart, such as: protection (e.g., from water absorption, ultra-violet damage), separation (e.g., chemical incompatibilities), altered release of active ingredients (e.g., immediate, extended, delayed, controlled release), and modification of sensory perception (e.g., smoothness/roughness, taste, color).

With titanium dioxide ($TiO_2$) becoming globally an unfavored colorant for a variety of reasons, the search for new or alternative components and ingredients that could replace the need and purpose of titanium dioxide has become crucial with respect to coatings within numerous industrial segments. The purpose of such new and alternative ingredients for titanium dioxide is specifically to increase the visual appeal, whiteness and brightness of substrates or substances such as tablets, capsules, granules, lozenges, candy or seeds that carry active ingredients such as agricultural, nutraceutical, and/or pharmaceutical active ingredients.

U.S. Pat. No. 4,931,286 (assigned to Aqualon company) discloses high gloss pharmaceutical tablets having an outer coating of sodium carboxymethyl cellulose and polyethylene glycol as 0.1 to 5.0% by weight of the tablet.

U.S. Pat. No. 10,159,650 (assigned to Sensient Colors LLC) discloses a film coating composition comprising hydroxypropyl methyl cellulose (HPMC), a cellulosic polymer, precipitated calcium carbonate, an opacifying agent, and a fatty acid.

However, it has been observed that sodium carboxymethyl cellulose (NaCMC) or precipitated calcium carbonate ($CaCO_3$) containing coating compositions of the prior art are not effective in providing good opacity and showed dull and greying appearance of the resulting coated products or substrates.

Therefore, there exists a need in the art for an effective whiter and brighter titanium dioxide free film coating composition that is suitable for coating solid substrates such as tablets, granules, lozenges, candy or seeds, that carry active ingredients, including but not limited to, agricultural, nutraceutical, and/or pharmaceutical actives.

Surprisingly and serendipitously, we have discovered a film coating composition free of titanium dioxide that provides (i) improved gloss and brighter appearance; and (ii) improved whiteness of coated solid substrates.

SUMMARY OF THE INVENTION

Improvements in film coatings have been discovered which impart better properties to the final or finished products than those of the prior art. These coatings comprise (i)

a water-soluble cellulose ether, (ii) a water-soluble anionic cellulose ether, (iii) calcium carbonate ($CaCO_3$), and (iv) a plasticizer.

In one aspect of the present invention, there is provided a titanium dioxide free white film coating composition comprising: (i) from 20 wt. % to 50 wt. % of hydroxypropyl methyl cellulose (HPMC), a water soluble cellulose ether; (ii) from 5 wt. % to 15 wt. % of carboxyl methyl cellulose (CMC), a water soluble anionic cellulose ether; (iii) from 10 wt. % to 60 wt. % of calcium carbonate ($CaCO_3$); and (iv) from 0.0 wt. % to 5 wt. % of a plasticizer.

According to another aspect of the present application, there is provided a white film coating composition having total solids content ranging from about 10 wt. % to about 25 wt. % of the total composition.

In another aspect, there is disclosed a colorant coating composition, wherein the composition further comprises from 0.001 wt. % to 25 wt. % of an optional secondary pigment, including but not limited to, red iron oxide, black iron oxide or combinations thereof.

In yet another aspect, there is disclosed a method of preparing a white film coated substrate, the method comprising the steps of: (a) preparing a coating suspension comprising the above-described white film coating composition, (b) applying the coating suspension of step (a) to the surface of the solid substrate to form a coating layer, (c) concurrently and/or thereafter drying said coating layer to form a dry coating on the surface of the solid substrate, and (d) obtaining the final film coated solid substrate.

According to another aspect, there is disclosed a white film coated solid product produced by a method comprising the steps of: (a) preparing a coating suspension comprising the above-described white film coating composition, (b) applying the coating suspension of step (a) to the surface of the solid product to form a coating layer, (c) concurrently and/or thereafter drying said coating layer to form a dry coating on the surface of the solid product, and (d) obtaining the desired final film coated solid product.

BRIEF DESCRIPTION OF THE DRAWINGS

Objects, features, and advantages of the present invention will become apparent upon reading the following description in conjunction with the drawings/figures, in which:

FIG. 7 is a Scanning Electron Microscopy image showing effect of particle size of calcium carbonate on coating opacity.

FIG. 8 is a picture of coated tablets showing effect of particle size of calcium carbonate on coating whiteness.

DETAILED DESCRIPTION OF THE INVENTION

Figure 1:
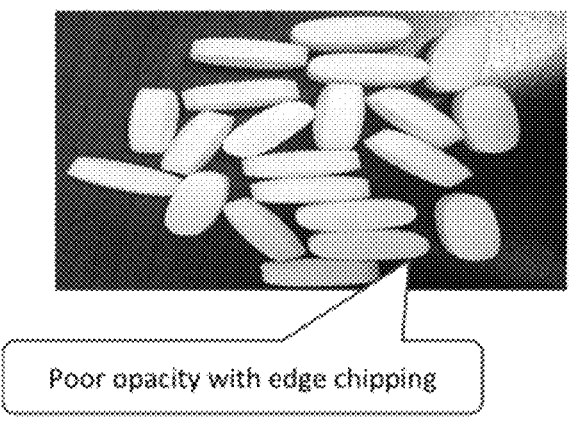
FIG. 1 depicts comparative tablets coated with hydroxypropyl methyl cellulose (HPMC) and hydroxypropyl cellulose (HPC) exhibiting poor opacity and dull appearance.

While this specification concludes with claims particularly pointing out and distinctly claiming that which is regarded as the invention, it is anticipated that the invention can be more readily understood through reading the following detailed description of the invention and study of the included examples.

As utilized in accordance with the disclosure, the following terms, unless otherwise indicated, shall be understood to have the following meaning.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

The singular forms "a," "an," and "the" include plural forms unless the context clearly dictates otherwise specified or clearly implied to the contrary by the context in which the reference is made. As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

For purposes of the following detailed description, other than in any operating examples, or where otherwise indicated, numbers that express, for example, quantities of ingredients used in the specification and claims are to be understood as being modified in all instances by the term "about". The numerical parameters set forth in the specification and attached claims are approximations that may vary depending upon the desired properties to be obtained in carrying out the invention.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All publications, articles, papers, patents, patent publications, and other references cited herein are hereby incorporated herein in their entireties for all purposes to the extent consistent with the disclosure herein.

The terms "applicant's coating", "trial sample" and "inventive coating" as used herein are interchangeable and refer to the currently claimed coating compositions. Similarly, the terms "solid substrate" and "solid substance" are interchangeable in the current application.

The term "HPC" as used herein refers to hydroxypropyl cellulose.

The term "HPMC" as used herein refers to hydroxypropyl methyl cellulose.

The term "MCT" as used herein refers to medium chain triglycerides.

The term "PEG" as used herein refers to polyethylene glycol.

The term "NaCMC" as used herein refers to sodium carboxy methyl cellulose.

The term "solid substrate" or "solid substance" or "solid product" as used herein refers to, but is not limited to, tablets, granules, lozenges, candy, seeds, etc.

The current application specifically describes a white film coating and products coated therewith that provide unique advantages or properties that are not found in the prior art. The coatings are based on a combination of a water-soluble cellulosic polymer, a water soluble anionic cellulosic polymer, calcium carbonate, a plasticizer and other optional ingredients. These coatings provide improved film coatings that are whiter, brighter and glossy in appearance as compared to existing coatings.

In one embodiment, the present application provides a titanium dioxide free white film coating composition comprising: (i) from 20 wt. % to 50 wt. % of hydroxypropyl methyl cellulose (HPMC), a water soluble cellulose ether; (ii) from 5 wt. % to 15 wt. % of carboxy methyl cellulose (CMC), a water soluble anionic cellulose ether; (iii) from 10 wt. % to 60 wt. % of calcium carbonate; and (iv) from 5 wt. % to 25 wt. % of a plasticizer.

Further, the white film coating composition comprises from 0.0 wt. % to 5 wt. % of medium chain triglycerides (MCT), and from 0.0 wt. % to 2 wt. % of citric acid monohydrate.

In another embodiment of the present application, the white Film coating composition has total solids content ranging from about 10 wt. % to about 25 wt. % of the total composition. In a non-limiting embodiment of the present application, other possible ranges of solid content would include, but are not limited to, from about 10 wt. % to about 15 wt. % of the total composition; from about 15 wt. % to about 20 wt. % of the total composition; or from about 20 wt. % to about 25 wt. % of the total composition.

In another embodiment, the water-soluble cellulose ether has a general structure as represented below:

wherein each $R_1$, $R_2$, $R_3$, $R_4$, $R_5$, and $R_6$ is/are independently substituted to form a cellulose ether derivative(s) with appropriate functional moieties. Examples of such derivatives include but not limited to carboxymethyl cellulose (CMC), hydroxyethyl cellulose (HEC), hydroxypropyl cellulose (HPC), hydroxypropyl methyl cellulose (HPMC) and methyl cellulose (MC). These cellulose ethers differ in terms of the various R functional groups, the degrees of hydroxyl groups substitution, and in their molecular weight ranges.

Hydroxypropyl methyl cellulose, is also known by its acronym HPMC and pharmaceutical grades are also known by the generic chemical name Hypromellose. HPMC is a partially O-methylated and O-(2-hydroxypropylated) cellulose, wherein $R_1$, $R_2$, $R_4$, and $R_5$ are OH, $OCH_3$, and/or $O[CH_3CH(OH)CH_2]y$; and $R_3$ and $R_6$ are $CH_2OH$, $CH_2OCH_3$ and/or $CH_2O[CH_3CH(OH)CH_2]_y$, where the subscript "y" represents the number of hydroxypropyl monomer units. For the purposes of present invention, the commercially available HPMC can be duly obtained from Dow Chemical (Methocel™ grades E3, E5, E6, E15, E50, E4M, E10M, F50, K3, K100, K4M, K15M, K100M), Shin-Etsu

US 12,599,566 B2

5
Chemical Company (Pharmacoat grades 603, 606, 615, 904), and Hercules Inc. (Benecel® MP 843, 814, and 844).

Hydroxypropyl methyl cellulose (HPMC)

The HPMC is present in an amount of 20-50%, preferably 20-45% and more preferably 25-45% by weight based on the total weight of the coating composition. Two or more different grades of HPMC can be present.

Hydroxypropyl cellulose (HPC) is a partially substituted poly(hydroxyethyl)ether of cellulose, wherein $R_1$, $R_2$, $R_4$, and $R_5$ are OH and/or $O[CH_2CH(CH_3)O]_y$ H; and $R_3$ and $R_6$ are $CH_2OH$ or $CH_2O[CH_2CH(CH_3)O]_y$ H, wherein subscript "y" represents that number of hydroxypropyl monomer units. HPC grades produced by Ashland LLC. include Klucel® EF, LF, HF, JF, LF, MF, GF;

Hydroxypropyl cellulose (HPC)

Sodium carboxymethyl cellulose (NaCMC) is a water soluble anionic cellulosic polymer. Carboxymethylcellulose sodium is a sodium salt of a polycarboxymethyl ether of cellulose, wherein $R_1$, $R_2$, $R_4$, and $R_5$ are OH; and $R_3$ and $R_6$ are $CH_2OCH_2COONa$. Commercially available NaCMC includes, but is not limited to, the trade names of Hercules Inc. Aqualon® and Blanose®. The chemical and physical properties of NaCMC find wider applications in food, pharmaceuticals and personal care, etc. Carboxymethyl cellulose has the following structure:

6

Carboxymethyl cellulose (CMC)

The CMC is present in an amount of 5-15%, 5-10% or 10-15% by weight based on the total weight of the coating composition. Two or more different grades of CMC can be present.

The calcium carbonate ($CaCO_3$) useful herein can be obtained from natural deposits, and thereafter is finely ground or is obtained via chemical precipitation and drying of the precipitate. Calcium carbonate is used as a filling material in paintings, rubber, paper, food, pharmacy, plastics and so on. Calcium carbonate is an opacifying agent and provides film coatings herein with excellent brightness, whiteness, and/or opacity without using compounds containing heavy metals. Precipitated calcium carbonate's morphology affords an increased surface area and disperses more uniformly in aqueous medium. Morphology and particle size of calcium carbonate affects the whiteness and opacity of film coatings. Calcium carbonate morphology include prismatic and scalenohedral structures. Particle size of calcium carbonate used in the present coating composition is selected from 0.5 microns to 20 microns. Accordingly, the particle size of the calcium carbonate can range from 0.5 microns to about 5 microns; from 5 microns to 10 microns; from 10 microns to 15 microns; from 15 microns to 20 microns. More preferably, the current application employs calcium carbonate with a mean particle size of 1.8 to 2.0 microns and scalenohedral morphology. The calcium carbonate is present in an amount of 10-60%, preferably 15-55% and more preferably 20-50% by weight of the composition. Blends of different particle sizes and morphologies are contemplated.

The plasticizer is present in the range of from about 5 wt. % to about 30 wt. % to increase plasticity or fluidity. The plasticizer enhances the plastic properties of the polymeric composition, for example, by increasing flexibility and/or durability by lowering the glass transition temperature (Tg) of the composition. Some plasticizers have been approved for direct or indirect human use through some end-user products. Examples of such plasticizers include citrates selected from acetyl tributyl, acetyl triethyl, tributyl and triethyl citrates; glycols selected from polyethylene glycol (PEG), propylene glycol and glycerin; phthalates selected from dibutyl, diethyl, and dimethyl phthalates: stearates selected from glyceryl monostearate; and triacetin. In one or more embodiments, the coating composition includes a PEG selected from the group including but not limited to PEG 200, PEG 300, PEG 400, PEG 600, PEG 1000, PEG 1500, PEG 4000, PEG 3350, PEG 6000 and PEG 8000. In another non-limiting embodiment of the present application, other possible ranges of plasticizers include, but are not limited to, from about 5 wt. % to about 10 wt. %; from about 10 wt. % to about 15 wt. %; from about 15 wt. % to about 20 wt. %; from about 20 wt. % to about 25 wt. %; or from about 25 wt. % to about 30 wt. %.

In another embodiment, the present application provides medium chain triglycerides (MCT), esters derived from glycerol and 3 fatty acids having a chain length of from 8 to 12 carbon atoms. The suitable fatty acid components are caprylic acid, capric acid, and lauric acid. Medium chain fatty acids with 8 carbon atoms can be referred to herein as C8 fatty acids or C8. The Medium chain fatty acids with 10 carbon atoms can be referred to herein as C10 fatty acids or C10. MCTs have been used in various applications such as food additives, treatment of neurological disorders, etc. The white film coating composition typically includes from 0.0 wt. % to 5 wt. % of medium chain triglycerides (MCT).

In another embodiment, the present application further provides citric acid either in the form of a monohydrate or an anhydrous form. Citric acid is widely used in pharmaceutical formulations and food products as an acidifying agent, an antioxidant, a buffering agent, a chelating agent or a favor enhancer. Citric acid monohydrate loses water on crystallization in dry air or when heated to about 40° C. The inventive film coating compositions can include from 0.0 wt. % to 2.0 wt. % of citric acid monohydrate.

Suitable pigments include colorants, dyes, and lakes, including, but not limited to, iron oxides, dyes such as for example, FD&C Lakes, Carmine Lake, FD&C Blue no. 1, FD&C Blue no. 2, FD&C Red no. 3, FD&C Red no. 40, FD&C Yellow no. 5, FD&C Yellow no. 6, FD&C Green no. 3, red iron oxide, black iron oxide, alumina talc, turmeric oleoresin, cochineal extract, *gardenia* yellow, *gardenia* blue, beet powder and the like. The pigment present in the inventive film coating composition of the present application can range from 0.001 wt. % to 25 wt. %, preferably 0.01 wt. % to 10 wt. % and can be selected from the group including, but not limited to, red iron oxide, black iron oxide or combinations thereof.

In another embodiment, the present application provides a coating preparation, wherein the ingredients are dry blended using commercial grade mixers, including high shear mixers. Solid ingredients such as polyethylene glycol (PEG) and medium chain triglycerides (MCT) can be used as plasticizers.

In another embodiment, the present application provides a method of preparing a white film coated solid substrate, the method comprising the steps of: (a) preparing a coating suspension comprising the white film coating composition described herein, (b) applying the coating suspension of step (a) to the surface of a solid substrate to form a coating layer, (c) concurrently or thereafter drying the coating layer to form a dry coating on the surface of the solid substrate, and (d) obtaining the final coated solid product or substrate.

In another embodiment, the solid coated substrate of the present application is an agricultural, a nutritional or a pharmaceutical product.

In another embodiment, the present application provides a coated pharmaceutical product or substrate formulated into an oral solid dosage form selected from tablets, minitablets, pellets, capsules, granules, lozenges, multi-particulates and the like.

In yet another embodiment, the present application provides a white film coated solid product produced by a method comprising the steps of: (a) preparing a coating suspension comprising the white film coating composition described herein, (b) applying the coating suspension of step (a) to the surface of the solid product to form a coating layer, (c) concurrently and/or thereafter drying said coating layer to form a dry coating on the surface of the solid product, and (d) obtaining the final film coated solid product.

In another embodiment, the present application provides a white film coated solid product or substrate, wherein the solid product or substrate is a coated agricultural product, a coated nutritional product or a coated pharmaceutical product. In a preferred embodiment, the white film coated pharmaceutical product is formulated into a pharmaceutical oral solid dosage form. Such forms include, but are not limited to, tablets, minitablets, pellets, capsules, granules, lozenges and multi-particulates.

In another embodiment, the present application provides titanium dioxide free coating systems with improved characteristics such as Gloss, Surface Roughness, Opacity and color resulting in maximizing product quality and enhancing processing efficiency.

Gloss

Figure 6:
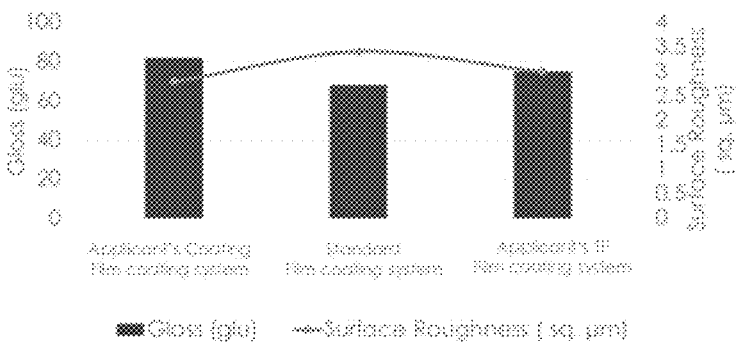
FIG. 6 is a graphical representation of Gloss and Surface Roughness parameters of applicant's film coatings and standard film coatings.

For the purpose of illustration and not as a limitation, Gloss of a tablet is measured by a Gloss meter/surface analysis system. Acceptable edges are clearly defined. Unacceptable edges are not defined. The current titanium dioxide free film coating systems imparts Gloss value of 80 Gloss Units (glu) measured against a standard of 60 glu. Results are shown in FIG. 6, which indicate that Gloss values are higher in applicant's coating compositions.

Surface Roughness

For the purpose of illustration and not as a limitation, roughness images are analyzed and corrected for surface curvature prior to determining the surface roughness, wherein shape of the form being removed should match the general shape of the tablet. The roughness for the sample set is reported as the average of the roughness values for the 16 tablets in the sample. Results are shown in FIG. 6. Roughness is shown to be around 2.5 square microns whereas the standard shows roughness values of 3 square microns which indicate that Surface roughness is reduced with current coating composition.

Color

Figure 3:
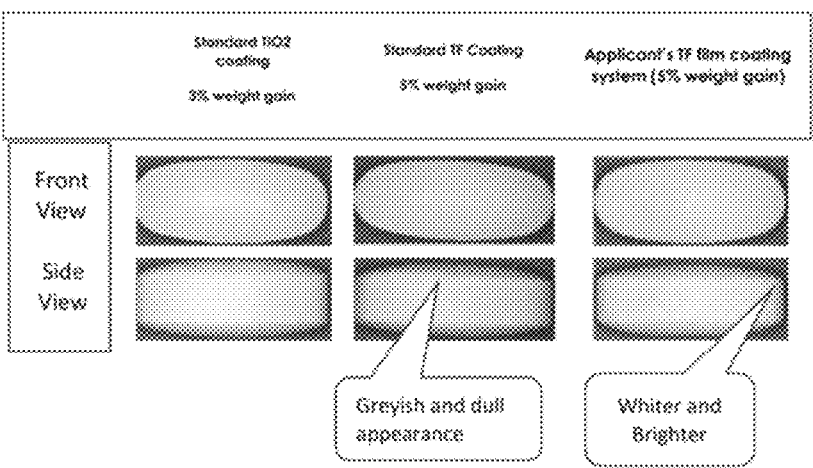
FIG. 3 is a front view of tablet whiteness showing images of prior art coatings (greyish and dull appearance) compared with applicant's coatings (whiter and brighter).
Figure 4:
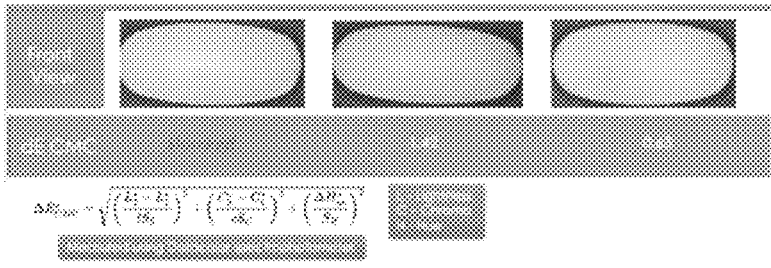
FIG. 4 is a front view of tablet whiteness comparison showing images of applicant's coated tablets versus a standard.
Figure 5:
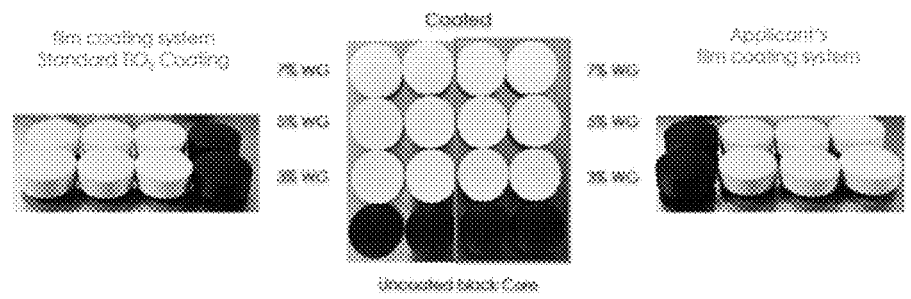
FIG. 5 is a picture showing opacity of applicant's film coatings and standard film coatings.

For the purpose of illustration and not as a limitation, color of a product is determined by reflectance measurement. Change in color has been visually analyzed and results are shown in FIG. 3, wherein applicant's film coatings are whiter and brighter with 5% weight gain. Change in color has been experimentally proved by measurement of reflectance by Data color spectrophotometer and results are shown in FIG. 4, wherein reflectance values are 0.63 for applicant's coating which is near to the standard coatings showing reflectance of 1.42. applicant's prime TF (titanium free) coating when applied to black colored tablets, turned white with 5% weight gain. The experimental results are presented in FIG. 5.

Opacity and Whiteness Coverage

For the purpose of illustration and not by way of limitation, Opacity is determined by Scanning Electron Microscopy (SEM), wherein higher the light reflectance, the more opaque is the film and more whiteness is imparted to the coated substrate. The results are shown in FIGS. 7 and 8.

In yet another embodiment of the present application, it has been discovered that the combination of cellulose ethers, calcium carbonate, plasticizer and other ingredients of the present application surprisingly increases the surface area capable of angular reflectance, increases the gloss, provides high opacity, brightness, and whiteness, reduces surface roughness to the coated substrate or product. These coating parameters for white film coatings along with standard coatings are provided in Table 9. Such film coatings that can be processed much more advantageously than would normally be expected by those skilled in the pertinent art, especially when compared to other types of coatings in the relevant arts. The whiteness and brightness are increased when compared to a traditional HPC based coating systems that are known in the arts for an artisan. Further benefits of these coating compositions are provided in the examples.

The examples that follow are aimed at illustrating the compositions and processes according to this invention but are not in any way a limitation of the scope of the invention.

EXAMPLES

Example 1: Coating Formula—A

A coating formula having a solid concentration range of 10%-15% was developed containing the ingredients hydroxy propyl methyl cellulose (HPMC), carboxy methyl cellulose (CMC), citric acid monohydrate and polyethylene glycol.

TABLE 1

| Coating Formulation A | |
| --- | --- |
| Formulation Ingredients | % w/w |
| Hydroxypropyl methyl cellulose (HPMC) type 2910 15 cP | 22.0 |
| Hydroxypropyl methyl cellulose (HPMC) type 2910 6 cP | 16.0 |
| Carboxymethyl cellulose 71.2P | 10.0 |
| Calcium Carbonate PCC | 39.0 |
| Citric Acid monohydrate | 1.0 |
| Polyethylene Glycol 3350 | 12.0 |
| Total | 100.0 |

Example 2: Coating Formula—B

A coating formula having a solid concentration range of 15%-20% was developed containing the ingredients three different ingredients of hydroxy propyl methyl cellulose (HPMC), carboxy methyl cellulose (CMC), citric acid monohydrate, medium chain triglycerides, and polyethylene glycol.

TABLE 2

| Coating Formulation B | |
| --- | --- |
| Formulation Ingredients | % w/w |
| Hydroxypropyl methyl cellulose (HPMC) type 2910 15 cP | 6.0 |
| Hydroxypropyl methyl cellulose (HPMC) type 2910 6 cP | 7.0 |
| Hydroxypropyl methyl cellulose (HPMC) type 2910 3 cP | 22.0 |
| Carboxymethyl cellulose 71.2P | 10.0 |
| Calcium Carbonate PCC | 38.0 |
| Citric Acid monohydrate | 1.0 |
| Medium chain triglycerides | 2.0 |
| Polyethylene Glycol 400 | 14.0 |
| Total | 100.0 |

Example 3: Coating Formula C

A coating formula was developed containing ingredients two different grades of hydroxy propyl methyl cellulose (HPMC), carboxy methyl cellulose (CMC), calcium carbonate, citric acid monohydrate, polyethylene glycol and medium chain triglyceride.

TABLE 3

| Coating Formulation C | |
| --- | --- |
| Formulation Ingredients | % w/w |
| Hydroxypropyl methyl cellulose (HPMC) type 2910 15 cP | 15.0 |
| Hydroxypropyl methyl cellulose (HPMC) type 2910 6 cP | 19.0 |
| Carboxymethyl cellulose 71.2P | 10.0 |
| Calcium Carbonate PCC | 35.0 |
| Citric Acid monohydrate | 1.0 |
| Polyethylene Glycol 400 | 19.0 |
| Medium chain triglyceride | 1.0 |
| Total | 100.0 |

Example 4: Coating Formula—D

A coating formula was developed containing the ingredients hydroxy propyl methyl cellulose (HPMC), carboxy methyl cellulose (CMC), calcium carbonate, citric acid monohydrate, polyethylene glycol and medium chain triglyceride.

TABLE 4

| Coating Formulation D | |
| --- | --- |
| Formulation Ingredients | % w/w |
| Hydroxypropyl methyl cellulose (HPMC) type 2910 15 cP | 20.0 |
| Carboxymethyl cellulose 71.2P | 10.0 |
| Calcium Carbonate PCC | 50.0 |
| Citric Acid monohydrate | 1.0 |
| Polyethylene Glycol 6000 | 18.0 |
| Medium chain triglyceride | 1.0 |
| Total | 100.0 |

Example 5: Coating Formula—E

A coating formula was developed containing two different grades of hydroxy propyl methyl cellulose (HPMC), carboxy methyl cellulose (CMC), calcium carbonate, and polyethylene glycol.

TABLE 5

| Coating Formulation E | |
| --- | --- |
| Formulation Ingredients | % w/w |
| Hydroxypropyl methyl cellulose (HPMC) type 2910 15 cP | 20.0 |
| Hydroxypropyl methyl cellulose (HPMC) type 2910 6 cP | 25.0 |
| Carboxymethyl cellulose 71.2P | 10.0 |
| Calcium Carbonate PCC | 20.0 |
| Polyethylene Glycol 400 | 25.0 |
| Total | 100.0 |

Example 6: Coating Formula—F

A coating formula was developed containing the ingredients hydroxy propyl methyl cellulose (HPMC), hydroxy ethyl cellulose (HEC), carboxy methyl cellulose (CMC), calcium carbonate, citric acid monohydrate, polyethylene glycol and medium chain triglyceride.

TABLE 6

| Coating Formulation F | |
| --- | --- |
| Formulation Ingredients | % w/w |
| Hydroxoxypropyl methyl cellulose (HPMC) type 2910 6 cP | 20.0 |
| Hydroxy ethyl cellulose (HEC) 250 L | 10.0 |
| Carboxymethyl cellulose 71.2P | 10.0 |
| Calcium Carbonate PCC | 46.0 |
| Citric Acid monohydrate | 1.0 |
| Polyethylene Glycol 3350 | 12.0 |
| Medium chain triglyceride | 1.0 |
| Total | 100.0 |

Example 7: Coating Formula—G

A coating formula having a solids concentration range of 15%-20% was developed containing three different grades of hydroxy propyl methyl cellulose (HPMC), carboxy methyl cellulose (CMC), calcium carbonate, red iron oxide, black iron oxide, citric acid monohydrate, medium chain triglycerides and polyethylene glycol.

TABLE 7

| Coating Formulation G | |
| --- | --- |
| Formulation Ingredients | % w/w |
| Hydroxypropyl methyl cellulose (HPMC) type 2910 15 cP | 6.0 |
| Hydroxypropyl methyl cellulose (HPMC) type 2910 6 cP | 7.0 |
| Hydroxypropyl methyl cellulose (HPMC) type 2910 3 cP | 22.0 |
| Carboxymethyl cellulose 71.2P | 10.0 |
| Calcium Carbonate PCC | 35.402 |
| Red Iron Oxide | 0.001 |
| Black Iron Oxide | 0.001 |
| Citric acid monohydrate | 1.0 |
| Medium chain triglycerides | 2.0 |
| Polyethylene Glycol 6000 | 14.0 |
| Total | 100.0 |

Example 8: Improvement in Color Uniformity

Figure 2:
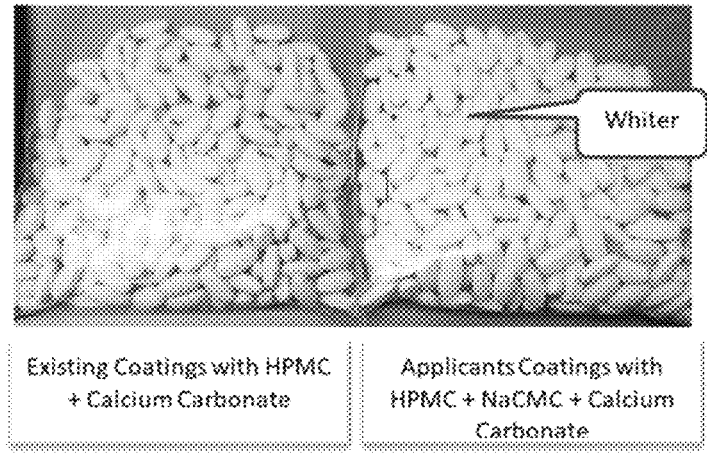
FIG. 2 shows images of prior art coatings compared with applicant's coatings which are whiter and brighter.

Placebo tablets were coated in a high speed run at 25% solids. It was observed that color uniformity improved when tablets were coated with white film coating compositions as formulated in Examples 1 to 8. Tablets subjected to applicant's coatings are whiter and brighter as shown in FIG. 1 and FIG. 2.

Example 9: Comparative Coating Formula Using Hydroxypropyl Cellulose

A coating formula was developed containing the ingredients hydroxy propyl cellulose (HPC), hydroxy propyl methyl cellulose (HPMC), carboxy methyl cellulose (CMC), calcium carbonate, yellow iron oxide, citric acid monohydrate, medium chain triglycerides and polyethylene glycol. Tablets coated with HPC showed poor opacity and edge chipping. Results are shown in FIG. 3.

TABLE 8

| Coating Formulation using HPC | |
| --- | --- |
| Formulation Ingredients | % w/w |
| Hydroxypropyl cellulose (HPC) ELF | 10.0 |
| Hydroxypropyl methyl cellulose (HPMC) type 2910 3 cP | 20.0 |
| Carboxymethyl cellulose 71.2P | 38.0 |
| Calcium Carbonate PCC | 36.7 |
| Yellow Iron Oxide | 0.89 |
| Citric acid monohydrate | 1.0 |
| Medium chain triglycerides | 2.0 |
| Polyethylene Glycol 3350 | 19.0 |
| Total | 100.0 |

Example 10: Better Opacity & Better Coverage of Whiteness

The white film coating opacity is typically resulting from the use of titanium dioxide because titanium dioxide, in its powdered form, provides the whitest and most highly opaque film with high refractive indices. Applicant's coating formula was developed using different particle sizes of calcium carbonate in combination with cellulose ethers to obtain the same opacity as in when titanium dioxide is used. Calcium carbonate with particle sizes 0.7 microns with prismatic structure and 1.8 microns and 2.0 microns with scalenohedral structure were tested. Smaller particle gives better coverage but, applicant's coating wherein, calcium carbonate with a larger mean particle size of 1.8-2.0 microns and scalenohedral structure were used, the final coatings showed better opacity and better coverage of whiteness compared to 0.7-micron prismatic calcium carbonate. The results are shown in FIGS. 7 and 8.

Example 11: Coating Attributes

TABLE 9

| | Coating Parameters | | |
| --- | --- | --- | --- |
| Attributes | SAMPLE -1 White film coating system | Standard TF White coating | SAMPLE - 2 White film coating system |
| AE | N/A | 1.42 | 0.63 |
| Opacity | ✓✓✓ | ✓ | ✓✓ |
| Brightness | +++ | + | ++ |
| Film Strength | ++ | + | + |
| Viscosity | 384 | 321 | 452 |
| Roughness | (2.8 μm) | (3.4 μm) | (3.0 μm) |

While the compositions and methods of the disclosed and/or claimed inventive concept(s) have been described in terms of particular aspects, it will be apparent to those of ordinary skill in the art that variations may be applied to the compositions and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

What is claimed is:

1. A titanium dioxide-free white film coating composition comprising:

(i) from 20 wt. % to 50 wt. % of hydroxypropyl methyl cellulose (HPMC), a water-soluble cellulose ether;

(ii) from 5 wt. % to 15 wt. % of carboxy methyl cellulose (CMC), a water soluble anionic cellulose ether;

(iii) from 10 wt. % to 60 wt. % of calcium carbonate ($CaCO_3$);

(iv) from 5 wt. % to 25 wt. % of a plasticizer;

(v) from 0.0 wt. % to 5 wt. % of medium chain triglycerides (MCT), and (vi) from 0.0 wt. % to 2 wt. % of citric acid monohydrate.

2. The titanium dioxide-free white film coating composition according to claim 1, wherein the composition has a total solids content ranging from about 10 wt. % to about 25 wt. %.

3. The titanium dioxide-free white film coating composition according to claim 1, wherein the plasticizer is polyethylene glycol (PEG).

4. A method of preparing a white film-coated substrate, the method comprising:

(a) creating a coating suspension comprising the titanium dioxide-free white film coating composition of claim 1;

(b) applying the coating suspension of step (a) to the surface of the solid substrate to form a coating layer;

(c) concurrently and/or thereafter drying said coating layer to form a dry coating on the surface of the solid substrate; and (d) obtaining the final white film-coated solid substrate.

5. The method according to claim 4, wherein said solid substrate is an agricultural product, a nutritional product, or a pharmaceutical product.

6. A white film-coated solid product produced by a method comprising the steps of:

(a) creating a coating suspension comprising the titanium dioxide-free white film coating composition of claim 1;

(b) applying the coating suspension of step (a) to the surface of the solid product to form a coating layer;

(c) concurrently and/or thereafter drying said coating layer to form a dry coating on the surface of the solid product; and (d) obtaining the final film-coated solid product.

7. The white film-coated solid product according to claim 6, wherein the white film-coated solid product is a coated agricultural product, a coated nutritional product, or a coated pharmaceutical product.

8. The white film-coated solid product according to claim 7, wherein the white film-coated solid product is a coated pharmaceutical product that is formulated into a pharmaceutical oral solid dosage form.

9. The white film-coated solid substrate according to claim 8, wherein the pharmaceutical oral solid dosage form is selected from the group consisting of tablets, capsules, granules, lozenges, candy, and seeds.

* * * * *